United States Patent [19]

Attali et al.

[11] Patent Number: 5,747,055
[45] Date of Patent: May 5, 1998

[54] INSECTICIDAL AND PESTICIDAL COMPLEX, AND METHOD FOR DESTROYING INSECTS AND ECTOPARASITES

[76] Inventors: Jean-Claude Attali, 5, chemin du Boudard, F-13260 Cassis; Jean-Claude Vuagnoux, Villa La Martine Plan des Moines, F-13390 Auriol, both of France

[21] Appl. No.: 666,546

[22] PCT Filed: Oct. 3, 1995

[86] PCT No.: PCT/FR95/01279

§ 371 Date: Jun. 10, 1996

§ 102(e) Date: Jun. 10, 1996

[87] PCT Pub. No.: WO96/10909

PCT Pub. Date: Apr. 18, 1996

[30] Foreign Application Priority Data

Oct. 10, 1994 [FR] France ................................. 94/12318

[51] Int. Cl.⁶ .................................................. A01N 25/08
[52] U.S. Cl. .......................... 424/409; 424/408; 424/411; 424/419; 424/421; 514/23
[58] Field of Search ............................. 424/405, 409, 424/411, 419, 421; 514/23

[56] References Cited

FOREIGN PATENT DOCUMENTS

| 0466986 | 1/1992 | European Pat. Off. |
| 2110524 | 6/1983 | United Kingdom . |

OTHER PUBLICATIONS

International Search Report and Annex.
Patent Abstracts of Japan, vol. 940, No. 010, accompanied by related Database WPI, Week 9444, Derwent Publications Ltd., AN 94-353784.

Patent Abstracts of Japan, vol. 016, No. 148 (Apr. 13, 1992).

Database WPI, Week 9222, Derwent Publications Ltd., AN 92-180839.

Chemical Abstracts, vol. 101, No. 17, Oct. 22, 1984, Abstract No. 149601, Green, "Abolition of Allergens by Tannic Acid", vol. 2, 8395, (1984), p. 160.

Naumann, *Chemistry of Plant Protection, vol. 4 Synthetic Pyrethroid Insecticides: Structures and Properties*, "3.4 Factors Enhancing the Action of Pyrethroids Against Arthropodpests", pp. 109-111 (1990).

Database WPI, Week 9138, Derwent Publications Ltd., AN 91-278132, accompanied by Patent Abstracts of Japan, of JP 184552 (Aug. 12, 1991).

Patent Abstracts of Japan, vol. 015, No. 478 (Dec. 4, 1991).

Database WPI, Week 8847, Derwent Publications Ltd., AN 88-335215.

Patent Abstracts of Japan, vol. 13, No. 182 (Apr. 27, 1989).

Patent Abstracts of Japan, vol. 15, No. 440 (Nov. 11, 1991).

*Primary Examiner*—Neil S. Levy
*Attorney, Agent, or Firm*—Greenblum & Bernstein P.L.C.

[57] ABSTRACT

An insecticidal and pesticidal complex including an active ingredient combined with an element to insert and diffuse the active ingredient within a vacuum cleaner dust bag. The element is shaped or sized such that it prevents the active ingredient and/or the element from clogging the permeable wall of the dust bag when the vacuum cleaner is in use. The active ingredient mainly includes a mixture of pesticides and insecticides, a growth hormone analogue, and a neutralizing agent.

20 Claims, No Drawings

INSECTICIDAL AND PESTICIDAL COMPLEX, AND METHOD FOR DESTROYING INSECTS AND ECTOPARASITES

BACKGROUND OF THE INVENTION

1. Field of the Invention

The present invention involves an insecticidal and pesticidal complex. It also involves a method for destroying insects and/or ectoparasites that proliferate in various spaces such as dwelling-places or the like, furniture, vehicles of all kinds, etc.

2. Discussion of Background

It is known, for example, that even in a perfectly maintained house, the dust found therein contains a large number of microscopic parasites such as dust mites, which are a main cause of respiratory and ocular allergies. These ectoparasites develop and are plentiful in beddings, mattresses, upholstery fabrics, carpets, closets, sofa cushions, curtains, as well as cracks in the ground and baseboards.

These mites, dead or alive, as well as their dejecta, i.e., freely constitute sensitizing allergens for respiratory systems. Thus, they cause a very large number of respiratory allergic ailments (asthma, rhinitis, spasmodic cough, in children and adults), as well as allergic conjunctivitis.

Furthermore, other types of ectoparasites and insects (fleas, ticks, lice, spiders, flies, mosquitoes, cockroaches, etc.) can be found, at various stages of reproduction or development (larvae, eggs, adults), in rugs, carpets, cracks in the floor, upholstery fabric fibers, etc., and likewise constitute causes for numerous allergic ailments and allergic conditions (dermatological allergies due to the inoculation of saliva through a flea bite, piroplasmosis caused by the ticks, paludism i.e., malaria, transmitted by the female anopheles mosquito, etc.).

The destruction of these insects and parasites in a residence is an important housekeeping task involving both and killing these insects and parasites, and to preventing their reproduction and propagation in the residence.

To this end, one is led to use a plurality of products at the same time, each product being specific to certain types of insects and parasites (crawling, flying, etc.). Based on their end-use, these products are packaged in the form of patches, platelets, powders, etc., to be placed in the areas of the residence assumed to be the most exposed and the most appropriate, or in the form of products to be spread throughout in the various rooms. The most commonly used method, to cover the largest area with pesticides and insecticides, consists of spreading these products (commercially available in the form of sprays) directly in the rooms to be protected or cleansed.

However, this "sanitation" method involves at least the following disadvantages:

the pulverized product does not disperse uniformly throughout the entire room, such that protection is ensured only in the areas where the product has settled;

the product can stain furniture with which it is in contact the household or industrial liquid aerosols, for spraying or nebulizing, must be used with caution (contact with mucous membranes and must be avoided, etc.);

pesticidal or insecticidal aerosols are often specific to a single type or category of insects or parasites, and it is necessary to use various aerosols at the same time to obtain the destruction of all the insects and parasites;

the product used in the aerosols makes it possible to kill certain parasites without suppressing the allergenic effect, still present and active, generated by their dead bodies.

Furthermore, the use of the various known products and methods for destroying insects and parasites does not suppress the daily obligation of cleaning the floors and of using a vacuum cleaner to remove dusts, stains, even ectoparasites and insects, that are found in the carpets, rugs, upholstery fabrics, or in inaccessible recesses of residences (cornices, baseboards) or of furniture (drawers, furniture bases).

It is well known that when using a vacuum cleaner, the air discharged can contain parasites which the porosity of the dust bag cannot stop, thus enabling them to spread once again. Furthermore, the dust bag of the vacuum cleaner is replaced only when it is full, i.e., about every two or three weeks and, meanwhile, the vacuum cleaner is stored in an area of the residence (cupboard, closet) where it constitutes a starting point for the reinfestation of the residence, in particular, by the mites that will proliferate in ideal conditions (dust and temperature) from said dust bag, and will then migrate outside toward new areas (clothing, fabrics, carpets).

SUMMARY OF THE INVENTION

Therefore, an object of the invention is to overcome the disadvantages of the pesticidal and insecticidal products and methods that are currently used in residences and others premises.

According to the invention, this goal is achieved by a pesticidal and insecticidal complex characterized by the fact that its active ingredient is combined with a means enabling the introduction and diffusion thereof within the dust bag of a vacuum cleaner, and is shaped or sized in such a way that it prevents said ingredient or said means from clogging the permeable bag wall when the vacuum cleaner is in use.

According to the method of the invention, the above-mentioned insecticidal or pesticidal complex is introduced in the dust bag of a vacuum cleaner, before the latter is used in all rooms and/or on all pieces or sets of furniture susceptible of containing, housing or sheltering mites or any types of noxious insects or parasites.

According to another characteristic arrangement of the invention, the active ingredient of the insecticidal and pesticidal complex mainly includes:

a mixture of pesticides and insecticides preferably constituted, at least for some of them, by pyrethrinoids;

a growth hormone analogue;

a neutralizing agent.

It is understood that during vacuum cleaning, the vacuum power removes the insects and parasites, drags them in the dust bag of the vacuum cleaner where they are killed by the pesticidal and insecticidal product deposited within said bag beforehand. The air exiting the vacuum cleaner, downstream of the dust bag, is cleared of the dust collected in the bag and, likewise, does not contain any parasites or insects, dead or alive. This prevents the parasites from spreading once again in the rooms of the residence or other locations, through the circulation of the air coming from the vacuum cleaner. In addition, the presence of said product in the dust bag makes it possible to avoid the multiplication and growth of parasites and insects within said bag.

The insecticidal and pesticidal complex and method according to the invention provide a plurality of advantages:

they are easy and quick to implement;

they do not cause any deterioration of the photosensitive insecticidal and pesticidal product that is kept away from light;

they make it possible to avoid any direct contact of the product with the furniture and/or with the person using the vacuum cleaner;

they do not cause any propagation or pollution of parasites during the discharge of air from the vacuum cleaner;

they prevent the vacuumed parasites and insects, present in the bag, from multiplying;

they make it possible to treat the entire surface of a room of a residence or any other premises in a single operation;

They cause the destruction of parasites by also removing their allergenic character.

Furthermore, due to the implementation of the product and method for destroying insects and parasites according to the invention, the traditional vacuum cleaner is no longer limited to the function of vacuuming dust and debris, but becomes a very efficient instrument for destroying parasites and insects.

The above-mentioned objects, characteristics and advantages, and more, will become more apparent from the description that follows.

DETAILED DESCRIPTION

The insecticidal and pesticidal product according to the invention includes:

1. an insecticidal and pesticidal ingredient;
2. a means allowing for the introduction and diffusion of this ingredient in the dust bag of a vacuum cleaner and preventing the clogging of the permeable wall of said bag.

In a very advantageous manner, the new insecticide and pesticide product used for implementing the complex and method according to the invention mainly includes:

1) a mixture of pesticides and insecticides;
2) a growth hormone analogue;
3) a neutralizing agent.

This product, very interestingly, includes the following constituents:

1) pyrethrinoids, preferably constituted by:
   a) tetramethrin or permethrin;
   b) cypermethrin.

2) a synergist such as piperonyl butoxide;

3) a growth hormone analogue, such as ovoprene, or methoprene, or ferroxycarb, or any other juvenile hormone analogue;

4) a neutralizing agent such as tannin, for example;

5) a scented excipient.

The association of tetramethrin and cypermethrin with complementary insecticidal spectra constitutes a redoubtable product for destroying parasites and insects, with a very substantial residual power of several weeks.

In addition, this action is synergized by the piperonyl butoxide.

The ovoprene becomes fixed on the fixing site of growth hormones, preventing the latter from playing its role. The growth hormone analogue causes a profound disorganization of the growth systems of parasites and insects, by blocking, in particular, the normal growth and development of the eggs and larvae that have been sucked in the vacuum cleaner dust bag, which prevents the normal and natural completion of the reproduction and metamorphosis cycle.

The neutralizing agent constituted by tannin acts by modifying the proteinic structures constituting the shells and bodies of the mites, by neutralizing these allergens and thus suppressing the origin of allergies caused by the bodies, even dead, of the vacuumed parasites.

The insecticidal and pesticidal product contains, for example, the above-mentioned ingredients in the following proportions:

pyrethrinoids (tetramethrin, permethrin, cypermethrin) 0.5–2% synergist (piperonyl butoxide) 2–4% growth hormone analogue (ovoprene) 0.1–0.2% neutralizing agent (tannin) 0.4–1% q.s.p. 100 g or 100 ml

The insecticidal and pesticidal complex formulated in the manner described previously, is more especially designed to have an efficient action with respect to a wide variety of insects and parasites, in a closed space in which it is adapted to be confined with the vacuumed insects and parasites.

The insecticidal and pesticidal complex can be presented in various forms: liquid, powder or solid; the means or vehicle enabling the introduction and diffusion of this product within the dust bag of a vacuum cleaner, differs depending upon the form of the product.

When it is presented in a powder form, the insecticidal and pesticidal complex can be enclosed in a small permeable bag, for example.

However, according to a very advantageous embodiment of the insecticidal and pesticidal complex according to the invention, the means that make it possible to avoid the clogging of the permeable walls of the dust bag of the vacuum cleaner, are constituted by particles or grains of inert solid matter (sand, glass balls, coal, cork, etc.) with a suitable particle size distribution and mixed with the insecticidal and pesticidal powder. These grains and particles have, for example, a diameter on the order of 1 mm or more.

Due to this constitution of the complex, a permanent mixing of the insecticidal powder is achieved by the agitation of the particles or grains created by the air draft resulting from the vacuum. Clogging of the permeable walls of the dust bag of a vacuum cleaner is thus avoided. Furthermore, a very intimate contact is also obtained between the active ingredients of the insecticidal and pesticidal powder and the insects and/or parasites collected with dust, which can only increase the efficiency of said active ingredients.

When the insecticidal and pesticidal complex is presented in a liquid form, for example, a solution, it can be contained in receptacles of various shapes and reduced dimensions, and arranged so as to allow for the slow evaporation of the product, for example: sticks, sponges, etc. which constitute different types of means and vehicles enabling the introduction and diffusion of the insecticidal product within the dust bag, and making it possible to avoid clogging the permeable wall thereof.

By way of a non-limiting example, this can be a small container made out of polyvinyl chloride PVC, in which a wick is plunged, which allows for the diffusion of the insecticidal and pesticidal product in the dust bag of a vacuum cleaner, by capillary action.

Whether it is formulated in a powder or liquid form, the insecticidal and pesticidal complex can be enclosed in a non-sealed container allowing for its diffusion outside said container, which constitutes the means that makes it possible to avoid clogging the permeable walls of the dust bag of a vacuum cleaner.

In any event, the insecticidal and pesticidal complex is presented in a volume that enables it to be placed in the bag of a vacuum cleaner, for example, by using the opening adapted to receive the base of the hose of a vacuum cleaner.

In a very advantageous manner, the liquid active ingredient can also impregnate pieces of porous or spongy solid matter of reduced dimensions (particles, grains, balls, etc.) whose particle size distribution or size is such that these particles cannot adhere to the permeable walls of the dust bag of the vacuum cleaner, said pieces of porous and spongy matter having a diameter on the order of 1 mm to a few centimeters.

It is readily understood now that the method for destroying insects and parasites present in a residence, or other locations and areas, according to the invention, consists of placing said insecticidal and pesticidal complex in the bag of a vacuum cleaner, then vacuuming the dust and debris as usual. According to the invention, no change occurs in the household routine, and the insects and parasites present in the residence are treated during the daily housekeeping. Each time the dust bag of the vacuum cleaner is replaced, a dose of said product is placed again in the new bag in order to renew the treatment.

The product according to the invention is placed in a dirt collecting bag, the photosensitive constituents of said product are thus kept away from light, which enables them to maintain their efficiency over time.

What is claimed:

1. A pesticidal complex, comprising:
   a liquid pesticidal active ingredient including:
      a mixture of pesticides including at least one pyrethrinoid;
      tannin;
      a growth hormone analogue comprising at least one member selected from the group consisting of ovoprene and methoprene; and
   a carrier comprising pieces of porous or spongy solid matter impregnated with the liquid pesticidal active ingredient, the carrier enabling introduction and diffusion of the liquid pesticidal active ingredient within a permeable dust bag of a vacuum cleaner, the carrier being shaped or sized such that the carrier prevents both the liquid pesticidal active ingredient and the carrier from clogging the permeable dust bag.

2. The pesticidal complex of claim 1, wherein the at least one pyrethrinoid includes tetramethrin and cypermethrin.

3. The pesticidal complex of claim 1, wherein the at least one pyrethrinoid includes permethrin and cypermethrin.

4. The pesticidal complex of claim 1, wherein the liquid pesticidal active ingredient further comprises a synergist.

5. The pesticidal complex of claim 4, wherein the synergist comprises piperonyl butoxide.

6. The pesticidal complex of claim 1, wherein the liquid pesticidal active ingredient further comprises a scented excipient.

7. A pesticidal complex, comprising:
   a powdered pesticidal active ingredient including:
      a mixture of pesticides including at least one pyrethrinoid;
      tannin;
      a growth hormone analogue comprising at least one member selected from the group consisting of ovoprene and methoprene; and
   a carrier comprising at least one member selected from the group consisting of sand, glass balls, coal, and cork having a size of at least 1 mm mixed with the powdered pesticidal active ingredient, the carrier enabling introduction and diffusion of the powdered pesticidal active ingredient within a permeable dust bag of a vacuum cleaner, the carrier being shaped or sized such that the carrier prevents both the powdered pesticidal active ingredient and the carrier from clogging the permeable dust bag.

8. The pesticidal complex of claim 7, wherein the at least one pyrethrinoid includes tetramethrin and cypermethrin.

9. The pesticidal complex of claim 7, wherein the at least one pyrethrinoid includes permethrin and cypermethrin.

10. The pesticidal complex of claim 7, wherein the powdered pesticidal active ingredient further comprises a synergist.

11. The pesticidal complex of claim 10, wherein the synergist comprises piperonyl butoxide.

12. The pesticidal complex of claim 1, wherein the powdered pesticidal active ingredient further comprises a scented excipient.

13. A pesticidal complex, comprising:
   a powdered pesticidal active ingredient including:
      a mixture of pesticides including at least one pyrethrinoid;
      tannin;
      a growth hormone analogue comprising at least one member selected from the group consisting of ovoprene and methoprene; and
   a carrier comprising a non-sealed container allowing for diffusion of the powdered pesticidal active ingredient to outside of the non-sealed container, the powdered pesticidal active ingredient being contained in the non-sealed container, the carrier enabling introduction and diffusion of the powdered pesticidal active ingredient within a permeable dust bag of a vacuum cleaner, the carrier being shaped or sized such that the carrier prevents both the powdered pesticidal active ingredient and the carrier from clogging the permeable dust bag.

14. The pesticidal complex of claim 13, wherein the at least one pyrethrinoid includes tetramethrin and cypermethrin.

15. The pesticidal complex of claim 13, wherein the at least one pyrethrinoid includes permethrin and cypermethrin.

16. The pesticidal complex of claim 13, wherein the powdered pesticidal active ingredient further comprises a synergist.

17. The pesticidal complex of claim 16, wherein the synergist comprises piperonyl butoxide.

18. The pesticidal complex of claim 13, wherein the powdered pesticidal active ingredient further comprises a scented excipient.

19. A method for destroying insects and parasites, comprising:
   introducing a pesticidal active ingredient into a dust bag of a vacuum cleaner, the pesticidal active ingredient including tannin, a mixture of pesticides including at least one pyrethrinoid, and a growth hormone analogue comprising at least one member selected from the group consisting of ovoprene and methoprene;
   after introducing the pesticidal active ingredient into the dust bag, vacuuming insects and parasites into the dust bag of the vacuum cleaner;
   preventing the insects and parasites from leaving the dust bag;
   destroying the insects and parasites through action of the mixture of pesticides; and
   modifying protein structures of casings and bodies of parasites to neutralize the casings and bodies from causing allergies.

20. The method of claim 19, wherein the pesticidal active ingredient is at least one of impregnated in, mixed with, and contained in a carrier enabling introduction and diffusion of the pesticidal active ingredient within the dust bag of the vacuum cleaner, the carrier being shaped or sized such that the carrier prevents both the pesticidal active ingredient and the carrier from clogging the dust bag.

* * * * *